United States Patent [19]

Jones et al.

[11] Patent Number: 4,737,595
[45] Date of Patent: Apr. 12, 1988

[54] HYDROCARBON DEHYDROGENATION

[75] Inventors: C. Andrew Jones, Newtown Square; John J. Leonard, Springfield; John A. Sofranko, Malvern, all of Pa.

[73] Assignee: Atlantic Richfield Company, Los Angeles, Calif.

[21] Appl. No.: 600,916

[22] Filed: Apr. 16, 1984

Related U.S. Application Data

[63] Continuation-in-part of Ser. No. 522,925, Aug. 12, 1983, Pat. No. 4,443,649, which is a continuation-in-part of Ser. No. 412,667, Aug. 30, 1982, abandoned, and a continuation-in-part of Ser. No. 522,944, Aug. 12, 1983, Pat. No. 4,444,984, which is a continuation-in-part of Ser. No. 412,655, Aug. 30, 1982, abandoned, and a continuation-in-part of Ser. No. 522,942, Aug. 12, 1983, Pat. No. 4,443,648, which is a continuation-in-part of Ser. No. 412,662, Aug. 30, 1982, abandoned, and a continuation-in-part of Ser. No. 522,905, Aug. 12, 1983, Pat. No. 4,443,645, which is a continuation-in-part of Ser No.412,663, Aug.,30,1982,abandoned, and a continuation-in-part of Ser. No. 522,877, Aug. 12, 1983, Pat. No. 4,443,647, which is a continuation-in-part of Ser. No. 412,664, Aug. 30, 1982, abandoned, and a continuation-in-part of Ser. No. 522,876, Aug. 12, 1983, Pat. No. 4,443,644, which is a continuation-in-part of Ser. No. 412,665, Aug. 30, 1982, abandoned, and a continuation-in-part of Ser. No. 522,906, Aug. 12, 1983, Pat. No. 4,443,646, which is a continuation-in-part of Ser. No. 412,666, Aug. 30, 1982, abandoned, and a continuation-in-part of Ser. No. 522,938, Aug. 12, 1983, Pat. No. 4,560,821, which is a continuation-in-part of Ser. No. 412,650, Aug. 30, 1982, abandoned.

[51] Int. Cl.$^4$ ............................................. C07C 5/327
[52] U.S. Cl. .................................. 585/654; 585/656; 585/658; 585/661; 585/444
[58] Field of Search ............... 585/654, 656, 658, 661, 585/444

[56] References Cited

U.S. PATENT DOCUMENTS

| | | | |
|---|---|---|---|
| 2,375,402 | 5/1945 | Corson et al. | 585/661 |
| 2,403,052 | 7/1946 | Cole et al. | 585/661 |
| 3,324,195 | 6/1967 | Hwa et al. | 585/658 |
| 3,336,408 | 8/1967 | Capp et al. | 585/444 |
| 3,410,920 | 11/1968 | Olson et al. | 585/656 |
| 3,513,216 | 5/1970 | Woskow | 585/656 |
| 3,585,248 | 6/1971 | Pasternak et al. | 585/658 |
| 3,682,838 | 8/1972 | Bloch | 585/656 |
| 3,845,156 | 10/1974 | Farha | 585/658 |
| 4,310,717 | 1/1982 | Eastman et al. | 585/661 |
| 4,368,346 | 1/1983 | Eastman | 585/658 |
| 4,454,363 | 1/1984 | Teng et al. | 585/435 |

*Primary Examiner*—William R. Dixon, Jr.
*Assistant Examiner*—Cynthia A. Prezlock
*Attorney, Agent, or Firm*—Craig E. Larson

[57] ABSTRACT

A method for dehydrogenating dehydrogenatable hydrocarbons which comprises contacting said hydrocarbons with a solid comprising at least one reducible oxide of at least one metal which oxides when contacted with hydrocarbons at the temperature are reduced and produce dehydrogenated hydrocarbon products and water, the solid being associated with a silica support. The oxide is reduced by the contact which is carried at about 500° to 100° C. The reducible metal oxides are regenerated by oxidizing the reduced composition with oxygen.

26 Claims, No Drawings

HYDROCARBON DEHYDROGENATION

CROSS REFERENCES TO RELATED APPLICATIONS

This application is a continuation-in-part of the following U.S. Patent Applications: (1) Application Ser. No. 522,925 filed Aug. 12, 1983, now U.S. Pat. No. 4,443,649 which in turn is a continuation-in-part of Application Ser. No. 412,667 filed Aug. 30, 1982, now abandoned; (2) Application Ser. No. 522,944 filed Aug. 12, 1983, now U.S. Pat. No. 4,444,984 which in turn is a continuation-in-part of Application Ser. No. 412,655 filed Aug. 30, 1982, now abandoned; (3) Application Ser. No. 522,942 filed Aug. 12, 1983, now U.S. Pat. No. 4,443,648 which in turn is a continuation-in-part of Application Ser. No. 412,662 filed Aug. 30, 1982, now abandoned; (4) Application Ser. No. 522,905 filed Aug. 12, 1983, now U.S. Pat. No. 4,463,645 which in turn is a continuation-in-part of Application Ser. No. 412,663 filed Aug. 30, 1982, now abandoned; (5) Application Ser. No. 522,877 filed Aug. 12, 1983, now U.S. Pat. No. 4,443,647 which in turn is a continuation-in-part of Application Ser. No. 412,664 filed Aug. 30, 1982, now abandoned; (6) Application Ser. No. 522,876 filed Aug. 12, 1983, now U.S. Pat. No. 4,443,644 which in turn is a continuation-in-part of Application Ser. No. 412,664 filed Aug. 30, 1982, now abandoned; (7) Application Ser. No. 522,906 filed Aug. 12, 1983, now U.S. Pat. No. 4,443,646 which in turn is a continuation-in-part of Application Ser. No. 412,666 filed Aug. 30, 1982, now abandoned; and (8) Application Ser. No. 522,938 filed Aug. 12, 1983, now U.S. Pat. No. 4,560,821 which in turn is a continuation-in-part of Application Ser. No. 412,650 filed Aug. 30, 1982, now abandoned. The entire content of these applications is incorporated herein by reference.

BACKGROUND OF THE INVENTION

This invention relates to dehydrogenation of dehydrogenatable hydrocarbons. This invention more particularly relates to oxidative dehydrogenation processes.

SUMMARY OF THE INVENTION

It has now been found that dehydrogenatable hydrocarbons may be dehydrogenated to dehydrogenated hydrocarbon products by containing a hydrocarbon containing gas with a solid comprising at least one reducible oxide of at least one metal which oxides when contacted with hydrocarbons at the temperature are reduced and produce dehydrogenated hydrocarbon products and water, the solid being associated with a support comprising $SiO_2$.

Dehydrogenatable hydrocarbons are desirably contacted with the solid at a temperature within the range of about 500° to 1000° C. The atomic ratio of metal of the reducable metal oxide to alkali metal is desirably within the range of about 1:1 to about 15:1. The metal oxide is reduced by contact with the hydrocarbon and is reoxidizable by contact with an oxygen-containing gas.

DETAILED DESCRIPTION OF THE INVENTION

Oxidative dehydrogenation agents are compositions comprising at least one oxide of at least one metal, which compositions, when contacted with a dehydrogenatable hydrocarbons (preferably at a temperature selected within the range of about 500° to 1000° C.), produces dehydrogenated hydrocarbons products, co-product water, and a composition comprising a reduced metal oxide. The composition thus contains at least one reducible oxide of at least one metal. The term "reducible" is used to identify those oxides of metals which are reduced by contact with dehydrogenatable hydrocarbons at elevated temperatures (preferably selected within the range of about 500° to 1000° C.). The term "oxide(s) of metal(s)" includes (1) one or more metal oxides (i.e., compounds described by the general formula $M_xO_y$ wherein M is a metal and the subscripts $x$ and $y$ designate the relative atomic proportions of metal and oxygen in the compound) and/or (2) one or more oxygen-containing metal compounds, provided that such oxides and compounds have the capability of performing to dehydrogenate dehydrogenatable hydrocarbons as set forth herein.

One class of preferred oxidative dehydrogenation agents comprises reducible oxides of metals selected from the group consisting of Mn, Sn, In, Ge, Sb, Pb, and Bi, and mixtures thereof. Particularly preferred oxidative dehydrogenation agents comprise a reducible oxide of manganese and mixtures of a reducible oxides of manganese with other oxidative dehydrogenation agents. More particularly preferred are reducible oxides of manganese associated with a silica support.

Other oxidative dehydrogenation agents may also be employed in the method of this invention, as will be apparent to one skilled in the art.

In the present invention, reducible oxides are provided as solid particles. They are supported by, or diluted with, the support material comprising silica.

Supported solids (i.e., particles) can be prepared by any suitable method. Conventional methods such as adsorption, impregnation, precipitation, coprecipitation, or dry-mixing can be used. A suitable method is to impregnate the support with solutions of compounds of the desired metal. Some examples of suitable compounds are the acetate, acetylacetonate, oxide, carbide, carbonate, hydroxide, formate, oxalate, nitrate, phosphate, sulfate, sulfide, tartrate, fluoride, chloride, bromide or iodide. After impregnation, the preparation is dried in an oven to remove solvent and the dried solid is prepared for use by calcining, preferably in air, at temperatures selected within the range of about 300° to 1200° C. Particular calcination temperatures will vary depending upon the particular metal compound.

Metal loadings on supported solids will generally be within the range of about 1 to 50 wt. % (calculated as the elemental metal(s) of the reducible oxides(s)).

The dehydrogenatable hydrocarbon feedstock employed in the method of this invention is intended to include a wide variety of hydrocarbons: e.g., $C_2+$ alkanes, cycloalkanes, olefins, alkylaromatics, etc. The dehydrogenated product will of course depend in part on the feedstock selected. For example, alkanes may be dehydrogenated to form olefins, diolefins, alkynes, etc., and olefins may be dehydrogenated to form diolefins, alkynes, etc. Thus, potential uses for the present process include the following conversions:

(1) ethane→ethylene→acetylene;
(2) propane→propylene;
(3) butane→butane→butadiene;
(4) 2-methylbutane→2-methylbutenes→isoprene; and
(5) toluene→stilbene.

One preferred class of feedstocks comprises $C_2$–$C_5$ alkanes.

Operating temperatures for the contacting of hydrocarbon-containing gas and the particles comprising an oxidative dehydrogenating agent are preferably selected from the range of about 500° to 1000° C.., the particular temperature selected depending upon the metal oxides employed in the oxidative dehydrogenation agent. For example, all oxidative dehydrogenation agents have the capability of dehydrogenating hydrocarbons when the temperature of the hydrocarbon contact is selected within the lower part of the recited range. Reducible oxides of certain metals, however, may require operating temperatures below the upper part of the recited range to minimize sublimation or volatilization of the metals (or compounds thereof) during hydrocarbon contact. Examples are: (1) reducible oxides of indium (operating temperatures will preferably not exceed about 850° C.); (2) reducible oxides of germanium (operating temperatures will preferably not exceed about 800° C.); and (3) reducible oxides of bismuth (operating temperatures will preferably not exceed about 850° C.).

Operating pressures for the hydrocarbon contacting step are not critical to the presently claimed invention.

Contacting hydrocarbon and an oxidative dehydrogenation agent to dehydrogenate dehydrogenatable hydrocarbons also reduces the oxidative dehydrogenation agent and produces coproduct water. The exact nature of the reduced forms of oxidative dehydrogenation agents are unknown, and so are referred to herein as "reduced dehydrogenation agent" or as "a reduced metal oxide." Regeneration of a reducible metal oxide is readily accomplished by contacting reduced compositions with oxygen (e.g., an oxygen-containing gas such as air) at a temperature selected within the range of about 300° to 1200° C., the particular temperature selected depending on the metal(s) included in the oxidative dehydrogenation agent.

In carrying out the present process, a single reactor apparatus containing a fixed bed of solids may be used with intermittent or pulsed flow of a first gas comprising dehydrogenatable hydrocarbon and a second gas comprising oxygen (e.g., oxygen, oxygen diluted with an inert gas, or air, preferably air). The hydrocarbon contacting step and the oxygen contacting step may also be performed in physically separate zones with solids recirculating between the two zones.

Thus, a suitable method for hydrogenating dehydrogenatable hydrocarbons comprises: (a) contacting a gas comprising said hydrocarbon and particles comprising a reducible metal oxide/and silica support to form dehydrogenated hydrocarbon products, co-product water, and reduced metal oxide; (b) removing particles comprising reduced metal oxide from the first zone and contacting the reduced particles in a second zone with an oxygen-containing gas to form particles comprising a reducible metal oxide and silica support; and (c) returning the particles produced in the second zone to the first zone. The steps are preferably repeated at least periodically, and more preferably the steps are continuous. In the more preferred embodiment solids are continuously circulated between at least one hydrocarbon-contact zone and at least one oxygen-contact zone.

Particles comprising a reducible metal oxide and silica support which are contacted with a dehydrogenatable hydrocarbon may be maintained as fluidized, ebullating, or entrained beds of solids. Preferably, the hydrocarbon is contacted with a fluidized bed of solids.

Similarly, particles comprising reduced metal oxide which are contacted with oxygen may be maintained as fluidized, ebullating or entrained beds of solids. Preferably oxygen is contacted with a fluidized bed of solids.

In one more preferred embodiment of the present invention, hydrocarbon feedstock and particles comprising a promoted oxidative dehydrogenation agent are continuously introduced into a hydrocarbon contact zone maintained at dehydrogenation conditions. Dehydrogenation conditions include the temperatures and pressures described above. Gaseous reaction products from the methane contact zone (separated from entrained solids) are further processed—e.g., they are passed through a fractionating system wherein the desired hydrocarbon products are separated from unconverted hydrocarbon and combustion products. Unconverted hydrocarbon may be recovered and recycled to the hydrocarbon contact zone.

Particles comprising reduced metal oxide are contacted with oxygen in an oxygen contact zone for a time sufficient to oxidize at least a portion of the reduced oxide to produce a reducible metal oxide and to remove, i.e., combust, at least a portion of any carbonaceous deposit which may form on the particles in the hydrocarbon contact zone. The conditions of the oxygen contact zone will preferably include a temperature selected within the range of about 300° to 1200° C., pressures of up to about 30 atmospheres, and average particle contact time within the range of about 1 to 120 minutes. Sufficient oxygen is preferably provided to oxidize all reduced metal oxide to produce a reducible oxide and to completly combust any carbonaceous deposit material deposited on the particles. At least a portion of the particles comprising promoted oxidative dehydrogenation agent which are produced in the oxygen contact zone are returned to the hydrocarbon contact zone.

The rate of solids withdrawal from the hydrocarbon contact zone is desirably balanced with the rate of solids passing from the oxygen contact zone to the hydrocarbon contact zone so as to maintain a substantially constant inventory of particles in the hydrocarbon contact zone, thereby enably steady state operation of the dehydrogenation system.

The invention is further illustrated by reference to the following examples.

Experimental results reported below include conversions and selectivities calculated on a carbon mole basis.

EXAMPLE I

A contact solid comprising a reducible oxide of manganese was prepared by impregnating Houdry HSC 534 silica with an aqueous solution containing of manganese and $Na_4P_2O_7$ in amounts sufficient to yield a solid containing 15 wt. % Mn/5% wt. % $Na_4P_2O_7/SiO_2$. The solids were dried at 150° C. for 2 hours and then calcined in air at 800° C. for 16 hours. A quartz tube reactor (12 min. inside diameter) was packed with 10 ml. of the calcined solids. The reactor was brought up to reaction temperature (indicated) under a flow of nitrogen. A feed of 100% ethane was then contacted with the solids at about atmospheric pressure and a GHSV (gas hourly spaced velocity) of 860 hr.−1. Cumulative samples of the effluent were taken and analyzed by gas chromatography and gas chromatography mass spectroscopy. Results are reported below in Table 1.

TABLE 1

| Temp. °C. | % Conversion | % Selectivity | | | | | | | |
|---|---|---|---|---|---|---|---|---|---|
| | | $CH_4$ | $C_2H_4$ | $C_3$ | $C_4$ | $C_5$ | CO | $CO_2$ | Coke |
| 700 | 24.2 | 2.0 | 91.9 | 1.1 | 2.4 | 0.05 | 0.54 | 1.9 | 0.03 |
| 800 | 78.2 | 10.0 | 76.0 | 2.8 | 4.1 | 0.68 | 1.6 | 1.5 | 0.16 |

EXAMPLE II

A contact solid comprising a reducible oxide of manganese was prepared by impregnating Houdry HSC 534 silica with an aqueous solution containing manganese and $Na_4P_2O_7$ in amounts sufficient to yield a solid containing 15 wt. % Mn/5 wt. % $Na_4P_2O_7/SiO_2$. The solids were dried at 150° C. for 2 hours and then calcined in air at 800° C. for 16 hours. A quartz tube reactor (12 min. inside diameter) was packed with 10 ml. of the calcined solids. The reactor was brought up to reaction temperature (indicated) under a flow of nitrogen. A feed of 100% propane was then contacted with the solids at about atmospheric pressure and a GHSV (gas hourly space velocity) of 857 hr.−1. Cumulative samples of the effluent were taken and analyzed by gas chromatography and gas chromatography mass spectroscopy. Results are reported below in Table 2.

TABLE 2

| Temp. °C. | % Conversion | % Selectivity | | | | | | | |
|---|---|---|---|---|---|---|---|---|---|
| | | $CH_4$ | $C_2H_4$ | $C_3$ | $C_4$ | $C_5$ | CO | $CO_2$ | Coke |
| 750 | 69.3 | 21 | 38 | 4 | 4 | 1 | 0.8 | 2 | 0.02 |
| 800 | 94.3 | 27 | 43 | 4 | 4 | 2 | 1 | 2 | 2 |
| 850 | 99.7 | 34 | 40 | 4 | 2 | 0.6 | 2 | 2 | 5 |

What is claimed is:

1. A method for dehydrogenating alkanes to form the corresponding olefins and coproduct water which comprises contacting at a temperature within the range of about 500°–1000° C. a gas comprising said alkanes and a solid comprising: (1) at least one reducible oxide of Ge, (2) at least one promoter selected from the group consisting of alkali metals and compounds thereof, and (3) a support silica.

2. The method of claim 1 wherein the alkali metal is selected from the group consisting of Li, Na, K, Rb, Cs, and compounds thereof.

3. The method of claim 2 wherein the alkali metal is selected from the group consisting of sodium, sodium compounds and mixtures thereof.

4. The method of claim 2 wherein the alkali metal is selected from the group consisting of potassium, potassium compounds and mixtures thereof.

5. The method of claim 2 wherein the alkali metal is selected from the group consisting of lithium, lithium compounds and mixtures thereof.

6. The method of claim 1 wherein said gas comprising alkanes comprises $C_2$–$C_5$ alkanes.

7. The method of claim 1 wherein the atomic ratio of Ge to said alkali promoter in said solid is within the range of between about 1:1 to about 15:1.

8. A method for dehydrogenating alkanes to form the corresponding olefins and coproduct water which comprises:
   (a) contacting at a temperature within the range of about 500°–1000° C. a gas comprising said alkanes and a solid comprising:
      (1) at least one reducible oxide of Ge,
      (2) at least one promoter selected from the group consisting of alkali metals and compounds thereof, and (3) a support comprising silica;
   (b) recovering dehydrogenated hydrocarbons;
   (c) at least periodically contacting solids comprising reduced Ge oxide with an oxygen-containing gas to produce a solid comprising a reducible oxide of Ge; and
   (d) contacting said solid produced in step (c) as recited in step (a).

9. The method of claim 8 wherein the temperature of step (c) is within the range of about 300° to 1200° C.

10. A method for dehydrogenating $C_2$–$C_5$ alkanes to form the corresponding olefins which comprises contacting at a temperature within the range of about 500°–1000° C. a gas comprising said alkanes and a solid consisting essentially of at least one reducible oxide of Sb with a support comprising silica.

11. The method of claim 10 wherein said solid further comprises a promoter selected from the group consisting of alkali metals and compounds thereof.

12. The method of claim 11 wherein the alkali metal is selected from the group consisting of Li, Na, K, Rb, Cs, and compounds thereof.

13. The method of claim 12 wherein the alkali metal is selected from the group consisting of sodium, sodium compounds and mixtures thereof.

14. The method of claim 12 wherein the alkali metal is selected from the group consisting of potassium, potassim compounds and mixtures thereof.

15. The method of claim 12 wherein the alkali metal is selected from the group consisting of lithium, lithium compounds and mixtures thereof.

16. The method of claim 11 wherein the atomic ratio of said metal to said alkali promoter in said solid is within the range of between about 1:1 to about 15:1.

17. A method for dehydrogenating alkanes to form the corresponding olefins which comprises contacting at a temperature within the range of about 500°–1000° C. a gas comprising said alkanes and a solid consisting essentially at least one reducible oxide of Bi with a support comprising silica.

18. The method of claim 17 wherein said solid further comprises a promoter selected from the group consisting of alkali metals and compounds thereof.

19. The method of claim 18 wherein the alkali metal is selected from the group consisting of Li, Na, K, Rb, Cs, and compounds thereof.

20. The method of claim 19 wherein the alkali metal is selected from the group consisting of sodium, sodium compounds and mixtures thereof.

21. The method of claim 19 wherein the alkali metal is selected from the group consisting of potassium, potassium compounds and mixtures thereof.

22. The method of claim 19 wherein the alkali metal is selected from the group consisting of lithium, lithium compounds and mixtures thereof.

23. The method of claim 17 wherein said gas comprising alkanes comprises $C_2$–$C_5$ alkanes.

24. The method of claim 18 wherein the atomic ratio of said metal to said alkali promoter in said solid is within the range of between about 1:1 to about 15:1.

25. A method for dehydrogenating alkanes to form the corresponding olefins which comprises:
   (a) contacting at a temperature within the range of about 500°–1000° C. a gas comprising said alkanes and a solid consisting essentially of at least one reducible oxide of Bi, associated with a support comprising silica;

(b) recovering dehydrogenated hydrocarbons;

(c) at least periodically contacting solids comprising reduced Bi oxide with an oxygen-containing gas to produce a solid comprising a reducible oxide of Bi; and (d) contacting said solid produced in step (c) as recited in step (a).

26. The method of claim 25 wherein the temperature of step (c) is within the range of about 300° to 1200° C.

* * * * *